United States Patent
Noda et al.

(10) Patent No.: US 6,534,197 B2
(45) Date of Patent: Mar. 18, 2003

(54) BIOMEDICAL IMPLANT MATERIAL AND METHOD OF PRODUCING THE SAME

(75) Inventors: Iwao Noda, Gamo-gun (JP); Junji Ikeda, Gamo-gun (JP); Takefumi Nakanishi, Gamo-gun (JP); Hiroyuki Kitano, Gamo-gun (JP); Shingo Masuda, Gamo-gun (JP)

(73) Assignee: Kyocera Corporation, Kyoto (JP)

( * ) Notice: Subject to any disclaimer, the term of this patent is extended or adjusted under 35 U.S.C. 154(b) by 0 days.

(21) Appl. No.: 09/818,054

(22) Filed: Mar. 26, 2001

(65) Prior Publication Data

US 2001/0036530 A1 Nov. 1, 2001

(30) Foreign Application Priority Data

Mar. 27, 2000 (JP) .......................................... 2000-087323

(51) Int. Cl.$^7$ ................................................. B32B 9/00
(52) U.S. Cl. ..................... 428/689; 427/2.26; 427/2.27; 433/201.1; 623/16.11; 623/18.11; 623/23.56; 623/23.51
(58) Field of Search ....................... 428/699; 433/201.1, 433/202.1; 623/11.11, 16.11, 18.11, 23.56, 23.57, 23.6, 23.61, 23.62; 427/2.1, 2.24, 2.26, 2.27

(56) References Cited

U.S. PATENT DOCUMENTS

| | | | | |
|---|---|---|---|---|
| 5,248,079 A | * | 9/1993 | Li | 228/121 |
| 5,397,362 A | * | 3/1995 | Noda | 623/23.56 |
| 6,299,438 B1 | * | 10/2001 | Sahagian et al. | 433/6 |

FOREIGN PATENT DOCUMENTS

| | | | | |
|---|---|---|---|---|
| JP | 59-46911 | | 11/1984 | |
| JP | 04-242659 | * | 8/1992 | ........... A61L/27/00 |
| JP | 6-233782 | | 8/1994 | |

* cited by examiner

Primary Examiner—Deborah Jones
Assistant Examiner—A B Sperty
(74) Attorney, Agent, or Firm—Hogan & Hartson, LLP

(57) ABSTRACT

The present invention provides a biomedical implant material comprising a substrate for biomedical implant made of a ceramic material, a first coating layer formed on the surface of said substrate by low-thermal impact coating process, and a second coating layer formed on said first coating layer via a metallic layer formed by thermal spraying process, and a method of producing the same. According to the biomedical implant material, it is made possible to prevent cracks from occurring in the ceramic substrate, and to secure sufficient bonding strength between the thermal-sprayed layer of titanium or the like onto the ceramic substrate.

8 Claims, 1 Drawing Sheet

BIOMEDICAL IMPLANT MATERIAL AND METHOD OF PRODUCING THE SAME

BACKGROUND OF THE INVENTION

The present invention relates to a biomedical implant material which constitutes an artificial bone or artificial joint used in orthopedic surgery of a patient having bone function or limb joint function lost due to a disease or a disaster, or an artificial tooth root used in a reconstructive surgery for a tooth lost due to aging or a disease, and a method of producing the same and, more particularly, to a biomedical implant material made of ceramics and a method of producing the same.

The field of implantology has been making remarkable advancements in recent years, and various artificial organs have been used in medicine such as artificial heart, artificial blood vessel and artificial lung. In the field of orthopedics, in particular, artificial joints are widely used for the restoration of joint functions that have been lost, while the artificial tooth root is attracting much attention in the field of dentistry.

Since intraosseous biomedical implants such as artificial joint, artificial bone and artificial tooth root must have high strength, such materials as stainless steel, cobalt-chromium alloy and titanium alloy have been mainly used, while ceramic materials have recently been used increasingly widely such as alumina and zirconia that have excellent corrosion resistance and sliding characteristic in the living body.

Such biomedical implants may be fixed in bone either by bonding to the bone by means of an acrylic resin called bone cement, or by making use of the restoring function of the patient's bone tissue in a practice called the cementless implant surgery. The former is simple and easily practiced with favorable result of fixation and allows the patient to leave the bed early, but involves the possibility of necrosis of the bone tissue due to the toxicity of acryl monomer and the heat generated during polymerization. The latter is free from the problem of toxicity and is regarded as a preferable method of fixation that is more compatible to the organism, and also because the natural function of the organism is made use of, but makes the surgical operation more difficult while stable fixation cannot be easily achieved.

In order to improve the intraosseous fixation of cementless implant, use of metallic implants with porous coating or hydroxyapatite coating applied to the surface thereof at the interface with the bone has recently been increasing, with satisfactory clinical results.

As to the biomedical implants made of ceramics, on the other hand, techniques of coating with calcium phosphate materials have been developed to improve the intraosseous fixation of cementless implant. For example, Japanese Published Examined Patent Application (Kokoku Tokkyo Koho Sho No.) 59-46911 discloses a technique of coating an implant made of ceramics with a calcium phosphate material by plasma spraying, and Japanese Published Unexamined Patent Application (Kokai Tokkyo Koho Hei No.) 6-233782 discloses a technique of providing a titanium thermal-sprayed layer as an intermediate layer between a ceramic implant and a calcium phosphate thermal-sprayed layer, although practically satisfactory results have not been achieved.

The former technique has such drawbacks as the calcium phosphate layer formed by thermal spraying has an insufficient strength of bonding to the base material of ceramics and the mechanical strength of the ceramic substrate decreases. The latter technique has a great effect of improving the bonding strength of the calcium phosphate thermal-sprayed layer, but often fails to achieve a satisfactory mechanical strength to counter the decrease in the strength of the ceramic substrate.

Reasons of the above problems will be described below.

In the case of the former technique, thermal spraying processes such as plasma spraying require a preliminary process such as sand blast to roughen the surface, but the ceramic substrate is too hard to roughen the surface thereof. As a result, sufficient bonding strength between the calcium phosphate thermal-sprayed layer and the implant can not be achieved. A ceramic material is also brittle and the mechanical strength thereof may be decreased significantly by even a small flaw on the surface thereof. Also the sand blast process described above is an effective method of roughening the surface of metallic materials which are ductile, but may be harmful to the ceramic materials.

In the case of the latter technique, the decrease in the strength of the ceramic substrate is caused by microscopic cracks generated in the ceramic substrate due to the difference in the thermal expansion coefficient between ceramics and titanium, thermal impact during thermal spraying and/or quick solidification and shrinkage of the titanium thermal-sprayed layer. While grooves may be formed on the ceramic substrate with this technique in order to achieve higher bonding strength between the ceramic substrate and the titanium thermal-sprayed layer, sufficient force of fixation may not be achieved depending on the direction of forming the grooves.

In light of the problems of the prior arts described above, an object of the present invention is to provide a biomedical implant material made of ceramics having a coating layer formed thereon with a sufficient bonding strength without decreasing the mechanical strength of the ceramic substrate, and a method of producing the same.

SUMMARY OF THE INVENTION

The present invention has been completed in order to solve the problems described above.

The present invention relates to a biomedical implant material comprising a substrate for biomedical implant made of a ceramic material, a first coating layer formed on the surface of said substrate by low-thermal impact coating process, and a second coating layer formed on said first coating layer via a metallic layer formed by thermal spraying process, and a method of producing a biomedical implant material, which comprises coating a substrate made of a ceramic material with titanium by the PVD (physical vapor deposition) process to form a titanium layer, thermal-spraying titanium on said titanium layer to form a titanium thermal-sprayed layer, and thermal-spraying a calcium phosphate layer on said titanium thermal-sprayed layer to form a calcium phosphate material layer.

The first coating layer of the biomedical implant of the present invention is formed by the low-thermal impact coating process, and is therefore provided without causing cracks in the substrate. The first coating layer has a function of shielding against the heat generated during thermal spraying of the metallic layer thereby protecting the substrate from significant thermal impact, and also serves as a bonding layer between the metallic layer and the ceramic substrate to hold both portions firmly together. This effect is achieved because, in contrast to a case of forming the metallic layer by the thermal spraying in which case the bonding strength between both members tends to be low as described above, the low-thermal impact coating process achieves high bonding strength and the bonding strength between the substrate and the metallic layer formed by the thermal spraying can be increased remarkably when the metallic layer is formed via the first coating layer by thermal spraying.

The biomedical implant material of the present invention also has the second coating layer formed via the metallic layer from the calcium phosphate material having the biocompatibility, with the surface thereof being roughened by thermal spray process (for example, plasma spraying or flame spraying), and therefore mechanical anchoring effect provides strong bonding force of the second coating layer to the first coating layer.

According to the present invention, since the intermediate layer (the first coating layer) is provided by the low-thermal impact coating process between the ceramic substrate and the thermal-sprayed layer made of titanium or the like (metallic layer), cracks are prevented from occurring in the ceramic substrate and sufficient bonding strength can be ensured between the thermal-sprayed layer made of titanium or the like and the ceramic substrate, thereby to provide a practically useful biomedical implant.

[DESCRIPTION OF REFERENCE NUMERALS]

Figure 1:
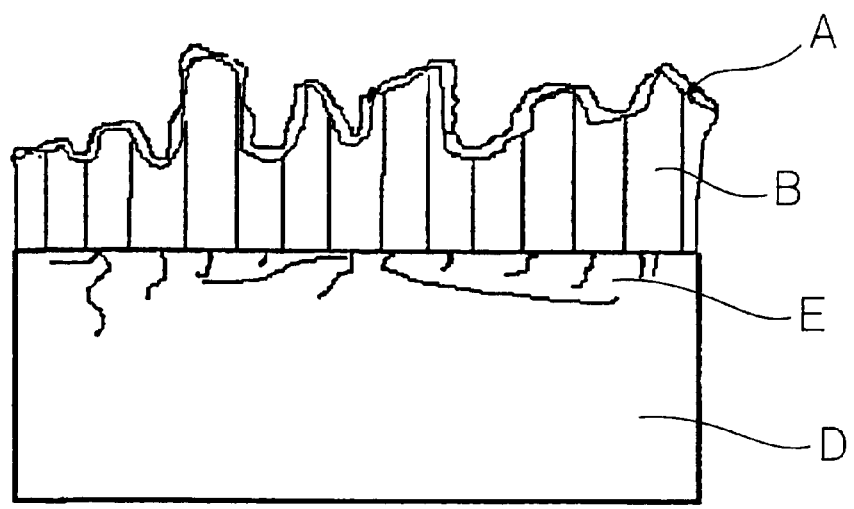
FIG. 1 is a schematic sectional view of a control in Example 1.

A: HA thermal-sprayed layer (second coating layer)
B: Titanium thermal-sprayed layer (metallic layer)
C: Titanium ion plating layer (first coating layer)
D: Zirconia substrate
E: Crack and lamination

DETAILED DESCRIPTION OF THE INVENTION

The embodiment of the biomedical implant material according to the present invention will now be described in detail below.

The biomedical implant material comprises a substrate for biomedical implant made of a ceramic material, a first coating layer formed on the surface of said substrate by low-thermal impact coating process, and a second coating layer formed on said first coating layer via a metallic layer formed by thermal spraying process.

As the ceramic substrate, a mixture of ceramic materials with increased material strength can be used such as oxide ceramics (alumina, zirconia and titania), nitride ceramics (silicon nitride, titanium nitride and aluminum nitride), carbide ceramics (silicon carbide), alumina-dispersed zirconia or titania-dispersed alumina.

Ion implantation may be applied to the ceramic substrate. Specifically, when ions of an element that constitutes the first coating layer are implanted in the ceramic substrate in advance, bonding of the first coating layer to the ceramic substrate can be improved. When titanium ions are implanted in the alumina substrate in advance, for example, the bonding strength can be increased by about 20% in case the first coating layer is formed by titanium coating.

Now the coating layer formed on the surface of the substrate will be described below.

The coating layer of the present invention is composed of three functional layers, that is, a first coating layer, a metal thermal spray layer, and a second coating layer.

First, the first coating layer will be described. The first coating layer may be constituted from the following material:

metal,
ceramic, or
metal+ceramics.

First, a case of forming the first coating layer from a metallic material will be described.

When the first coating layer is a single metallic layer, it is made of any one of titanium, tantalum, tungsten, zirconium, molybdenum, niobium, aluminum, silicon, gold, silver and palladium, an alloy containing them as a principal component, a cobalt-chromium alloy and a stainless steel; or a mixture of two or more kinds of them. In case the first coating layer is plural metallic layers, a combination of two or more kinds of them, or a combination of two or more mixtures of them is used.

In case a metallic layer is used as the first coating layer, improvement in the wettability of the ceramic substrate to the metal as a basic function of the plural metallic layers thereby to greatly improve the bonding to the metallic layer is obtained as the greatest merit. A merit of using a plurality of layers is that the bonding can be improved further by combining the materials having superior affinity with each other. In case the substrate is made of zirconia and the metallic layer is made of titanium, for example, stronger bonding can be achieved by using plural layers of zirconium and titanium for the first coating layer, than using a single layer of zirconium or titanium. Of course, zirconium is used on the substrate made of zirconia and titanium is used on the metallic (titanium) layer side. Also in the case of using a composite layer in part or the whole of the plural layers, interlayer bonding can be improved as the affinity between the materials of adjacent layers made of similar materials is improved.

The first coating layer may also be formed from ceramics. In this case, a single layer made of any one of alumina, zirconia, titania, silica, silicon carbide, silicon nitride, titanium nitride, aluminum nitride and TiCN or a mixture of two or more kinds of them, or plural layers made of two or more kinds of them, or two or more kinds of mixtures may be used. In case a ceramic layer is used as the first coating layer, an effect of shielding the thermal impact and impinging shock of the sprayed particles is obtained as the greatest merit. Since a ceramic layer has excellent heat resistance and hardness, the first coating layer made of ceramics can better endure the thermal impact caused by thermal spraying of the metallic layer and impinging shock of the sprayed particles, than in the case of constituting the first coating layer from a metal.

In order to improve the bonding performance of the ceramic layer to the ceramic substrate, plural ceramic layers or a mixture layer may be used. For example, in the case of a biomedical implant material made of zirconia substrate with a metallic layer of titanium alloy formed thereon, bonding performance can be improved by the affinity of the materials containing the same elements by forming the first coating layer from a mixture of titania and zirconia.

The first coating layer may also be constituted from plural layers made of the metallic material and the ceramic material, or from plural layers made of a mixture of these materials, thereby to combine the advantages of the metallic layer and the ceramic layer. That is, the first coating layer may have the effect of the metallic layer to improve the bonding strength and the effect of the ceramic layer to prevent cracks. In a bonding strength test, improvements in the bonding strength by an average of approximately 20% were observed when such composite layers or mixtures are used. Improvement in the effect of crack prevention is also observed, though in a qualitative evaluation through observation with a metallurgical microscope.

The first coating layer may also be formed by changing the proportions of the ceramic material and the metallic material gradually in the direction of the thickness of the layer.

When a biomedical implant substrate made of titanium nitride is coated with a titanium layer, for example, the first coating layer may be formed from titanium nitride and titanium by changing the proportions thereof gradually. This can be achieved by the ion plating process while flowing much nitrogen gas in the first stage to form a titanium nitride layer on the substrate made of titanium nitride, then gradually decreasing the quantity of the nitrogen gas to change the composition of the titanium nitride and titanium in the mixture layer, eventually stopping the nitrogen gas to make the layer surface consisting of titanium only. This makes it possible to increase the bonding strength of the thermally sprayed titanium layer by at least 30%.

The present invention is characterized by the low-thermal impact coating process employed when forming the first coating layer. The low thermal impact means that no significant thermal impact is applied to the base material whereon the coating layer is formed, specifically the ceramic substrate, or that stress due to shrinkage is not generated when the coating layer is cooled down. The coating layer may be formed by a PVD process such as vacuum deposition, ion beam deposition, sputtering, ion plating and dynamic mixing, CVD (chemical vapor deposition) process of TiCN or TiC, or wet coating process such as electroplating or electroless plating. A combination of these processes may also be used. For example, after vacuum deposition of silica on a biomedical implant substrate made of silicon nitride, titanium coating may be applied thereon by electroplating thereby to form the first coating layer. Among these, sputtering and ion plating are preferable in view of the bonding strength and uniformity of the coating layer and the production cost.

The first coating layer has the effect of shielding the heat during thermal spraying for forming the metallic layer thereby preventing significant thermal impact from being applied to the substrate, and the effect of holding the metallic layer firmly onto the substrate as bonding layer. The first coating layer itself is formed by the low-thermal impact coating process, and therefore can be provided without causing cracks in the substrate.

Now the metallic layer will be described below.

The metallic layer may be a single layer of a metal such as titanium, tantalum, tungsten, zirconium, molybdenum and niobium that have no toxicity for the organism or an alloy that includes some of these elements as a principal component, for example titanium alloy (Ti-6Al-4V; an alloy including 90% titanium, 6% aluminum and 4% vanadium), or an alloy of medical use such as cobalt-chromium alloy or stainless steel formed by thermal spraying.

Since the second coating layer is eluted and is substituted by the bone tissue over time, the metallic layer makes direct contact with the bone tissue in the long term. Therefore, the metallic layer must consist of a biocompatible material that has been proved to be safe in the living body.

The thermal spray may also be applied, besides individual thermal spraying of any one of the materials described above, by spraying two or more materials at the same time to form a layer of mixture, in which case higher bonding to the underlying first coating layer may be achieved. In case the first coating layer is made of titania, better bonding tends to be achieved by forming this metallic layer from a mixture of zirconium and titania, than in the case of forming this metallic layer from zirconium only. This is because of the affinity between titania and titanium.

The metallic layer is preferably formed by a thermal spraying process wherein contact with the atmosphere and a reactive gas is avoided, such as shield arc spraying, low pressure arc spraying, low pressure plasma spraying and low pressure laser spraying, in order to prevent chemical reaction such as oxidation and nitration from occurring during the thermal spraying process. Since a thermal spraying process that is capable of completely shutting off the chemical reaction such as oxidation is not commercially available at present, reaction of a certain extent cannot be avoided. However, inclusion of oxygen and/or nitrogen by 30% or more decreases the ductility of the metallic film and makes it brittle, and should be avoided. This is because brittleness gives rise to the possibility of the coating layer to partially come off during surgical operation and the destruction of the coating layer over time.

The metallic layer serves as a bonding layer for the second coating layer to be formed thereon. In case the metallic layer is formed by thermal spraying of titanium, for example, sufficient bonding strength of hydroxyapatite (hereinafter referred to as HA) can be obtained by applying sand blast to the surface of the titanium thermal-sprayed layer and applying the thermal spray of HA to form the second coating layer. The sand blast treatment does not affect the ceramic substrate and therefore does not decrease the mechanical strength thereof. In case a ceramic material is used for the metallic layer, the result becomes the same as that of the thermal spraying of HA to the ceramic substrate, thus making it impossible to ensure a sufficient bonding strength of the HA layer. This is the reason why ceramics cannot be used for the metallic layer.

The reason for forming the metallic layer by the thermal spraying process is because this gives the metallic layer very high surface roughness enough to maintain a sufficient force of fixing the cementless implant in the bone through ingrowth of the bone tissue even after the calcium phosphate layer has been eluted out in the living body. The surface roughness is required to be 10 $\mu$m or higher in terms of maximum surface roughness (Rmax) in order to achieve sufficient intraosseous fixation. A value of Rmax higher than 2000 $\mu$m leads to a decrease in the thermal-sprayed layer and particularly in the mechanical strength of protruding portion, and is not desirable. At present, the only coating process capable of achieving such a high level of surface roughness and a strong bonding force, at the same time, is the thermal spraying process. Thus the metallic layer has surface roughness high enough to allow the ingrowth of the bone tissue in the cementless implant, and one of important functions of the metallic layer is to greatly assist the fixation of the cementless implant in the bone.

Now the second coating layer will be described below.

This layer is formed on the metallic layer by such processes as the thermal spraying, deposition or application coating. The layer may be formed from calcium phosphate materials including calcium phosphate crystalline materials such as hydroxyapatite (HA), tri calcium phosphate (TCP) and octa calcium phosphate (OCP), calcium phosphate glass ceramics such as apatite wollastonite glass ceramics (AWGC), calcium phosphate composite ceramics such as apatite composite ceramics (ACC) or amorphous calcium phosphate. The second coating layer may also be formed from an organic material such as chitin and chitosan which have high affinity with the bone. This layer may be constituted either as a single layer of one material selected from among the materials described above, plural layers of two or more kinds of materials, or a composite layer of two or more kinds of materials. For example, the second coating layer may be formed by plasma spraying of HA. The HA layer may also be coated thereon with TCP by the same plasma spraying. Or, alternatively, a coating layer of a mixture of TCP and HA may also be formed by the plasma spraying process.

The second coating layer may be formed by such processes, in addition to the thermal spraying including flame spraying, plasma spraying, high-speed flame spraying, explosion spraying and laser spraying, as alkali heat treatment, deposition process such as biomimetic technique and application coating such as dipping. These processes may also be combined. For example, after coating with HA by high-speed flame spraying, TCP coating may be provided by dipping process.

Thermal spraying is the most practically useful technique used widely in coating with HA. The alkali heat treatment process, wherein a metallic layer made of titanium or the like that has been dipped in an alkali solution is subjected to heat treatment in atmosphere so that HA deposits on the surface of the metallic layer after being implanted in a human body, can be conveniently practiced and is competitive in terms of cost. The same can be said also for the biomimetic technique wherein a metallic layer is dipped in a simulated body fluid that includes phosphate ion or calcium ion so that HA is deposited directly on the surface of the metallic layer.

The application coating method, wherein an implant is dipped in a slurry prepared by kneading a mixture of calcium phosphate such as TCP, water and a binder, so as to be coated with calcium phosphate by applying drying and firing as required, has such a merit as the implant can be coated with a calcium phosphate layer of high crystallinity more easily with a lower cost than the thermal spraying process.

The second coating layer is formed on the outermost layer of the interface of the biomedical implant with the bone, and has a function of promoting the ingrowth of the bone tissue into the porous layer in the cementless implant. This is due to the excellent permittivity of the calcium phosphate material to the bone tissue. While HA is most commonly used as the calcium phosphate material, coating with TCP or amorphous calcium phosphate having higher elution rate may also be employed to ensure earlier fixation in the bone. However, since TCP and similar materials tend to disappear fast in line with the fast elution, it is better to employ the plural layers or the mixed layer of HA and TCP described previously for safety, in the case of a patient who has such an unfavorable bone characteristics as the normal ingrowth of bone tissue cannot be expected.

With regards to the biomedical implant material constituted as described above, thickness and surface roughness of the coating layers will be described below.

While thickness of the coating layer varies depending on the material and the coating process employed, thickness of the first coating layer is preferably from 0.001 mm to 1.0 mm. When the thickness is less than 0.001 mm, sufficient effect of preventing cracks cannot be expected. When the thickness is greater than 1.0 mm, there arises a possibility of intralayer destruction in the ceramic layer. Thickness of the metallic layer is preferably from 0.01 mm to 3.0 mm. When the thickness is less than 0.01 mm, it is difficult to obtain a surface having maximum surface roughness (Rmax) of 10 $\mu$m or higher that is required to achieve intraosseous fixation. When the thickness is greater than 3.0 mm, bonding strength of the layer may decrease due to residual stress.

The thickness of the second coating layer is preferably from 0.001 mm to 2 mm. When the thickness is less than 0.001 mm, the film diminishes too fast in the organism and has no practical value. When the thickness is greater than 2 mm, there arises a possibility of intralayer destruction of the calcium phosphate material layer.

As to the surface roughness of the coating layers, the first coating layer preferably has a value of Rmax within 200 $\mu$m as described previously. When Rmax is greater than 200 $\mu$m, an effect similar to that of sand blast is produced thus resulting in the decreasing mechanical strength of the ceramic substrate. The metallic layer preferably has a value of Rmax from 10 $\mu$m up to 2000 $\mu$m. This is because 10 $\mu$m is the lower limit for the surface roughness to be capable of securing intraosseous fixation, while strength of the thermal-sprayed layer, particularly of the projecting portions decreases when the value of Rmax is greater than 2000 $\mu$m.

The following Examples further illustrate the present invention in detail below.

EXAMPLE 1

Ceramic circular disks made of zirconia measuring 17 mm in diameter and 5 mm in thickness were washed to degrease, and were coated on one side thereof on one circular side of a diameter of 17 mm thereof with titanium to a thickness of 20 $\mu$m by ion plating. Then thermal spraying of titanium was applied by the shield arc spraying to a thickness of 500 $\mu$m, and an HA layer having a thickness of 20 $\mu$m was formed thereon by flame spraying, thereby to make test pieces for experiment. The test pieces were subjected to the observation of cut surface and to bonding strength test. The observation of cut surface was conducted by means of a metallurgical microscope (400 times magnification) after embedding the test piece in a resin, cutting and polishing the cut surface. The bonding strength test was conducted in accordance with a procedure specified in JIS H8666 (Ceramic thermal spray test method). Each test piece was held on a testing fixture with an epoxy adhesive applied on both sides thereof. Then rupture strength was measured by applying a load at a stretching speed of 1 mm/minute until the test piece was broken with an Intron tensile testing machine (Instron Inc.). Each test piece was observed on the rupture surface by naked eyes and an optical microscope. Control test pieces without the ion plating layer formed thereon were made for comparative evaluation.

The test results are shown in Table 1.

TABLE 1

| Test piece | Observation of cut surface (n = 3) | Bonding strength test (n = 5) |
|---|---|---|
| Test piece group of the present invention (ion plating layer provided) | No crack observed | 67 MPa in average |

TABLE 1-continued

| Test piece | Observation of cut surface (n = 3) | Bonding strength test (n = 5) |
|---|---|---|
| Control group (without ion plating layer) | Many cracks observed. Lamination occurred in zirconia layer. | 41 MPa in average |

Figure 2:
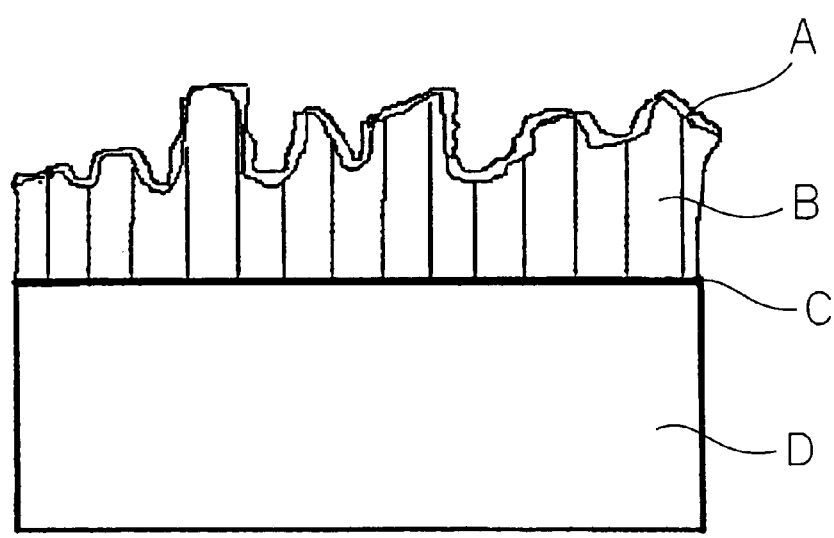
FIG. 2 is a schematic sectional view of a test piece of the present invention in Example 1.

The test pieces of the present invention were made by coating implant bodies made of zirconia ceramics with ion plating layer of titanium as the first coating layer, forming titanium layer thereon by thermal spraying as the metallic layer, and forming the second coating layer on the metallic layer by thermal spraying of HA. In the test, many cracks and lamination were observed in the cut surface of the control group, while the test pieces of the present invention did not show any crack. Cut surfaces are shown schematically in FIG. 1 for the control group and in FIG. 2 for the test pieces of the present invention. In the bonding strength test, the test pieces of the present invention showed a high mean bonding strength of 67 MPa, while that of the control group was 41 MPa.

EXAMPLE 2

Cylindrical test pieces made of alumina ceramics measuring 6 mm in diameter and 20 mm in length were coated on the circumferential surface thereof with a titanium nitride layer having thickness of 10 μm by the sputtering process, and low pressure plasma spraying of titanium nitride and titanium was applied by graded composition method. Thickness of the thermal-sprayed layer is 600 μm, with the first coating layer being formed from titanium nitride and the metallic layer being formed from titanium. The test pieces were immersed in a simulated body fluid for 24 hours, so that an apatite crystal layer having thickness of 2 μm was deposited on the surface of the titanium layer. The test piece was implanted in a drilled hole of the diaphysis of a femur of a grown-up mongrel dog, with the dog being killed after eight weeks of the surgical operation and subjected to push-out test. Control test pieces (group C-1) made of alumina ceramics and control (group C-2) without titanium nitride coating layer being sputtered thereon were made and subjected to the experiment at the same time. Each group comprised five test pieces.

The test results are shown in Table 2.

TABLE 2

| Test piece | Rupture strength (MPa) | Breaking position |
|---|---|---|
| Test pieces of the invention | 25.5 | Within bone |
| Control group C-1 | 0.5 | Bone-test piece interface |
| Control group C-2 | 18.2 | Alumina-thermal sprayed layer interface |

The test pieces of the invention was made by coating a biomedical implant substrate made of alumina ceramics with a titanium nitride layer by the sputtering process thereby to form the first coating layer, forming plural layers of titanium nitride and titanium by the low pressure plasma spraying as the metallic layer, and forming the apatite crystal layer by deposition process. In the animal experiment, bonding with the bone was hardly achieved with the test pieces of the control group C-1 made solely of alumina, while the test pieces of the control group C-2 showed a force of intraosseous fixation 36 times higher than that of the control group C-1. However, test pieces of the control group C-2 ruptured in the interface between the alumina and the thermal-sprayed layer, namely inside of the implant, indicating that the coating layer did not have sufficient bonding strength for a practical implant. In contrast, the test pieces of the invention not only showed rupture strength of a value as high as 25.5 MPa but also experienced breakage within the bone, and proved to be biomedical implant material of high performance having a force of intraosseous fixation sufficient for a cementless implant and a sufficient bonding strength of the coating layer.

What is claimed is:

1. A biomedical implant material comprising:

a substrate for biomedical implant including a ceramic material, a first coating layer on the surface of said substrate, said first coating layer formed by a low-thermal impact coating process, a metallic layer on said first coating layer, said metallic layer being formed by a thermal spraying process, and a second coating layer on said metallic layer.

2. The biomedical implant material according to claim 1, wherein said ceramic material includes one or more materials selected from the group consisting of alumina, zirconia, titania, silicon nitride, silicon carbide, titanium nitride and aluminum nitride.

3. The biomedical implant material according to claim 1, wherein said low-thermal impact coating process is a PVD process, a CVD process or a plating process.

4. The biomedical implant material according to claim 3, wherein said first coating layer is composed of a single layer of a ceramic material or plural layers including the ceramic material.

5. The biomedical implant material according to claim 3, wherein said first coating layer includes a metal.

6. A biomedical implant material comprising:

a substrate for biomedical implant including a ceramic material, a first coating layer on the surface of said substrate, said first coating layer formed by a low-thermal impact coating process, a metallic layer on said first coating layer, said metallic layer being formed by a thermal spraying process, and a second coating layer on said metallic layer, wherein said first coating layer includes a mixed phase of a metal and a ceramic material.

7. The biomedical implant material according to claim 1, wherein said metallic layer includes one or more materials selected from the group consisting of titanium, tantalum, tungsten, zirconium, molybdenum and niobium, an alloy containing them as a principal component, a cobalt-chromium alloy and a stainless steel; or a mixture of two or more kinds of them.

8. The biomedical implant material according to claim 1, wherein said second coating layer includes a calcium phosphate material.

* * * * *